(12) United States Patent
Fritze et al.

(10) Patent No.: US 9,339,359 B2
(45) Date of Patent: May 17, 2016

(54) APPLICATOR INSTRUMENT FOR DENTAL COMPOUNDS

(71) Applicant: Gilltec GmbH, Kiel (DE)

(72) Inventors: Joachim Fritze, Bad Bramstedt (DE); Jochen Heinz, Flintbek (DE); Philipp Rolle, Neumenster (DE)

(73) Assignee: Gilltec GmbH, Kiel (DE)

( * ) Notice: Subject to any disclaimer, the term of this patent is extended or adjusted under 35 U.S.C. 154(b) by 19 days.

(21) Appl. No.: 14/109,073

(22) Filed: Dec. 17, 2013

(65) Prior Publication Data

US 2014/0106301 A1    Apr. 17, 2014

Related U.S. Application Data

(63) Continuation of application No. 12/722,076, filed on Mar. 11, 2010, now Pat. No. 8,622,643.

(30) Foreign Application Priority Data

Mar. 23, 2009  (DE) .......................... 10 2009 014 446
Feb. 22, 2010  (EP) ..................................... 10001753

(51) Int. Cl.
*A46B 3/22* (2006.01)
*A61C 19/06* (2006.01)
(Continued)

(52) U.S. Cl.
CPC ................. *A61C 19/063* (2013.01); *A46B 3/22* (2013.01); *A46B 9/005* (2013.01); *A61C 3/005* (2013.01); *A61C 5/062* (2013.01)

(58) Field of Classification Search
CPC ............. A46B 3/22; A46B 2200/1066; A46B 2200/1073; A46B 2200/108; A61C 19/063

USPC ................... 15/104.93, 106; 221/286, 312 A; 222/421, 629; 449/49, 61; 73/864, 73/864.71, 864.72; 401/126; 433/141
See application file for complete search history.

(56) References Cited

U.S. PATENT DOCUMENTS 2,545,814 A *  3/1951  Kempster .......................... 15/188
4,527,575 A *  7/1985  Vasas ............................. 132/218
(Continued)

FOREIGN PATENT DOCUMENTS

DE    199 34 235    10/2000
DE    600 32 814    11/2007
(Continued)

OTHER PUBLICATIONS

European Search Report mailed Jul. 26, 2010, directed towards European Application No. 10001753.2; 3 pages.
(Continued)

*Primary Examiner* — Jennifer C Chiang
*Assistant Examiner* — Joshua Wiljanen
(74) *Attorney, Agent, or Firm* — Morrison & Foerster LLP

(57) ABSTRACT

The invention relates to an applicator instrument for applying dental compounds. The applicator instrument comprises an instrument head with a support structure and with a plurality of projections formed on the support structure. The projections are elastic and, in relation to a height extent, have less stiffness than the support structure. Between them, the projections enclose a receiving space for the dental compound. According to the invention, the projections have a planar configuration and, in relation to a width extent, are arranged substantially parallel to one another. The greatest diameter of the instrument head is between 2 mm and 3 mm. With the applicator instrument according to the invention, it is easier to apply the dental compound in dosed amounts and to spread the dental compound across the surface that is to be treated.

16 Claims, 6 Drawing Sheets

(51) Int. Cl.
*A46B 9/00* (2006.01)
*A61C 3/00* (2006.01)
*A61C 5/06* (2006.01)

(56) References Cited

U.S. PATENT DOCUMENTS

| | | | | |
|---|---|---|---|---|
| 5,896,614 | A * | 4/1999 | Flewitt | 15/167.1 |
| 6,010,265 | A * | 1/2000 | Bouix | 401/122 |
| 6,067,684 | A * | 5/2000 | Kweon | 15/167.1 |
| 6,571,417 | B1 * | 6/2003 | Gavney et al. | 15/117 |
| 6,634,051 | B1 | 10/2003 | Dragan et al. | |
| 6,767,209 | B1 | 7/2004 | Tomita et al. | |
| 6,957,958 | B2 | 10/2005 | Rowe et al. | |
| 7,143,462 | B2 * | 12/2006 | Hohlbein | 15/111 |
| 7,827,998 | B2 * | 11/2010 | Rebours | 132/218 |
| 2002/0020424 | A1 | 2/2002 | Gueret | |
| 2004/0031114 | A1 | 2/2004 | Dragan et al. | |
| 2004/0197730 | A1 | 10/2004 | Rowe et al. | |

FOREIGN PATENT DOCUMENTS

| | | |
|---|---|---|
| EP | 1 147 746 | 10/2001 |
| EP | 1 258 227 | 11/2002 |
| EP | 1 259 186 | 11/2002 |

OTHER PUBLICATIONS

"AdHoc Honigloeffel," located at http://kuechenhelfer-kochgeschirr.de/p6517/adhoc-honigloeffel.html visited on Aug. 20, 2009. 2 pages.

Fritze et al., U.S. Office Action mailed Dec. 6, 2012, directed to U.S. Appl. No. 12/722,076; 7 pages.

Fritze et al., U.S. Office Action mailed May 2, 2013, directed to U.S. Appl. No. 12/722,076; 7 pages.

* cited by examiner

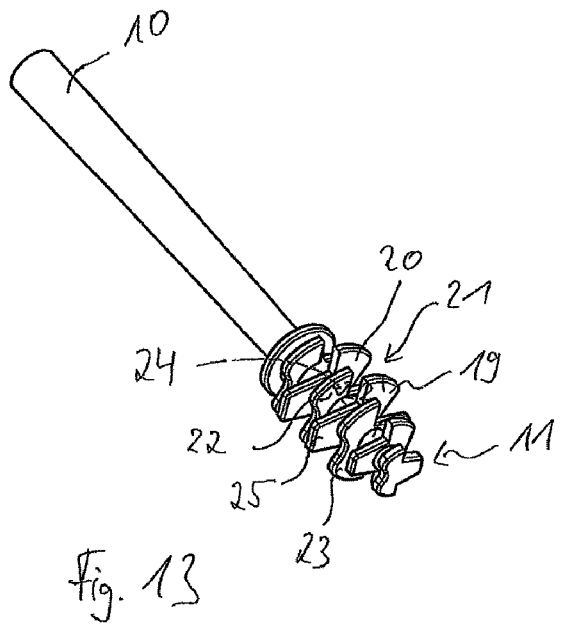
Fig. 13
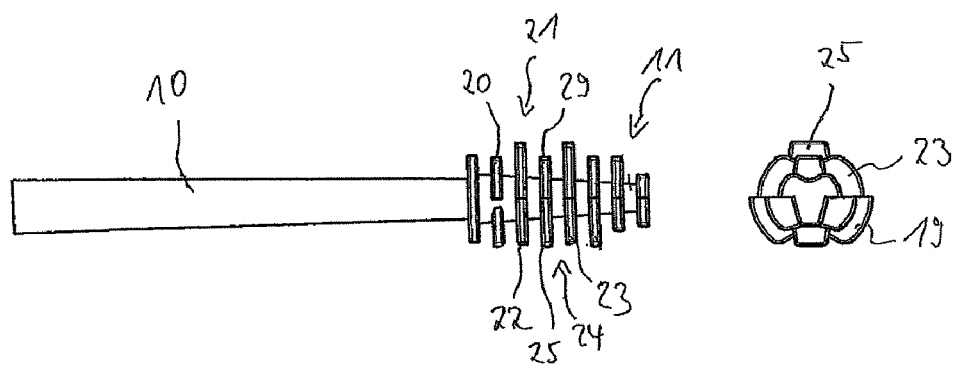
Fig. 14
Fig. 15

APPLICATOR INSTRUMENT FOR DENTAL COMPOUNDS

REFERENCE TO RELATED APPLICATIONS

This application is a continuation of U.S. patent application Ser. No. 12/722,076, filed Mar. 11, 2010, U.S. Pat. No. 8,622,643, which claims the priority of German Patent Application No. 10 2009 014 446.3, filed Mar. 23, 2009, and European Patent Application No. 10001753.2, filed Feb. 22, 2010, the contents of which prior applications are incorporated herein by reference.

FIELD OF THE INVENTION

The invention relates to an applicator instrument for applying dental compounds. The applicator instrument comprises an instrument head with a support structure and with a plurality of projections formed on the support structure. The projections are elastic and, in relation to a height extent, have less stiffness than the support structure. Between them, the projections enclose a receiving space for the dental compound.

BACKGROUND OF THE INVENTION

Conventional instruments for applying dental compounds to a surface that is to be treated have the form of a brush. A multiplicity of bristles, which are secured on an instrument head, lie so close together that they are able to hold the dental compound between them. The instrument head is immersed into a container with the dental compound, such that the bristles can take up the dental compound. On the surface that is to be treated, the dental compound is pressed out of the applicator instrument and spread across the surface to be treated, for example a hole in a tooth. In brushes of this kind, the bristles are mounted on the instrument head in a separate production step. They are therefore relatively expensive to produce and cannot be miniaturized to an unlimited extent. Conventional brushes are often too large for the minimally invasive treatment of teeth that is customary today.

In the meantime, microbrushes have become widely used in which the front end has substantially radially oriented fibers affixed to it. The fibers are very thin and have low inherent stability. This has the effect that, in relation to the volume of the instrument head, a large amount of dental compound can be taken up and the dental compound can be easily pressed out of the fibers. However, it is not entirely easy to spread the dispensed dental compound across the surface that is to be treated, because each forward and backward stroke with the microbrush leads to further amounts of dental compound emerging from the microbrush and being applied to the surface. For the same reason, it is not easy to apply a precisely dosed amount of dental compound to the surface.

SUMMARY OF THE INVENTION

The object of the invention is to make available a technically improved applicator instrument which, in particular, is more user-friendly. Proceeding from the prior art mentioned at the outset, the object is achieved by the features broadly disclosed herein. Advantageous embodiments are set forth in the disclosure. According to the invention, the projections have a planar configuration and, in relation to a width extent, are arranged substantially parallel to one another. The greatest diameter of the instrument head is preferably between 2 mm and 3 mm.

A number of terms will first be explained. The height extent of a projection denotes the direction in which the projections extend away from the support structure. The width extent runs perpendicular thereto. The projections have less stiffness than the support structure when a force can be exerted on the projections via the support structure, such that the projections deform in relation to their height extent. Details concerning the diameter of the instrument head relate to a diameter oriented transverse to the lengthwise direction of the instrument head.

A receiving space within the meaning of the invention is delimited on two sides by surfaces of the projections. In this context, a plurality of projections is also referred to when the surfaces of the two projections are connected by an intermediate piece, for example a spiral-shaped intermediate piece. Between the projections, there are outlet areas in which the receiving space opens without further restriction into the surrounding environment. Upon suitable deformation of the planar projections, the volume of the receiving space decreases, and dental compound contained in the receiving space emerges from the receiving space via the outlet areas.

When the applicator instrument according to the invention is immersed into a dental compound, the receiving space fills with the dental compound. The receiving space is so dimensioned, and adapted to the dental compound, that the dental compound remains in the receiving space when the applicator instrument re-emerges from the dental compound. On the surface that is to be treated, pressure is exerted on the planar projections by way of the support structure, such that the planar projections deform and the volume of the receiving space decreases. The dental compound emerges from the receiving space and adheres on the relevant part of the surface that is to be treated. Since the geometric shape of the receiving space is known and a precisely defined deformation takes place, the dental compound to be dispensed can be precisely dosed. After the projections have been relieved of pressure again and have assumed their original shape, the projections are used to spread the dental compound across the surface. The projections have sufficient stiffness to allow the dental compound to be spread across the surface without further dental compound emerging from the receiving space. The applicator instrument thus offers a high degree of user friendliness.

In its simplest embodiment, the applicator instrument according to the invention has only two projections and one receiving space arranged between the projections. A more uniform spread of the dental compound is possible by having several receiving spaces arranged next to one another. For this purpose, more than two planar projections are arranged substantially parallel to one another, such that a central planar projection separates two adjacent receiving spaces from each other. The distance between two planar projections is preferably smaller than the greatest height extent of the projections. The projections can then be deformed such that they lie directly on each other. The volume of the receiving space decreases to almost zero, and the dental compound can be dispensed almost completely from the receiving space and applied to the surface.

The applicator instrument according to the invention preferably comprises a shaft, the proximal end of which is designed as a grip part. The distal end of the shaft is connected fixedly or releasably to the instrument head. The shaft and the connection to the instrument head are so stable that a force sufficient to deform the planar projections can be transferred to the instrument head.

In one embodiment, the height extent of the planar projections runs substantially in the continuation of the shaft. The dental compound can then be pressed out of the receiving space by pressure being exerted in the longitudinal direction of the shaft, and it can be spread across the surface by means of movements in the transverse direction thereto.

In other embodiments, the height extent of the planar projections runs substantially radially in relation to the direction of the shaft. The width extent of the projections can in this case be oriented substantially transverse or substantially parallel to the direction of the shaft.

The applicator instrument according to the invention is intended in particular to be used for applying dental compounds in holes that are to be filled in teeth. For this purpose, the greatest diameter of the instrument head is preferably less than 5 mm, more preferably less than 3 mm. It is also helpful if the instrument head is adapted in terms of its contour to the shape of the hole. In particular, the instrument head can have a spherical contour, or a cylindrical contour in which the axis is oriented substantially parallel to the direction of the shaft. This can be achieved if the applicator instrument has the following features either singly or in combination. The support structure can have a planar configuration and thus provide a surface along which the projections can, in relation to their width extent, be oriented transverse to the direction of the shaft. It is possible to provide a first set and a second set of projections, which are arranged on opposite sides of the planar support structure. The projections can, in relation to their height extent, run substantially perpendicular to the surface of the support structure. The planar form of the support structure can be approximated to a circle shape. At the center of the support structure, projections can be formed which have a greater height extent than do projections at the edge of the support structure. The contour of the projections can be approximated to the shape of a segment of a circle.

It is desirable that, in relation to the size of the instrument head, as much dental compound as possible can be taken up and dispensed within the tooth. In relation to the volume encompassed by the instrument head, the receiving spaces preferably take up at least 40%, more preferably at least 60%. The volume of the projections is preferably small compared to the volume of the receiving spaces. The distance between two projections that between them enclose a receiving space is preferably greater than the material thickness of the projections.

Receiving spaces of large volume can be achieved in particular if the projections that between them enclose the receiving space are at a great distance from each other. However, if the distance of the projections from each other is too great, there is a danger of the dental compound no longer being held safely in the receiving space. In order to give the dental compound more hold, a first receiving space and a second receiving space can be offset relative to each other in such a way that a projection of the first receiving space is arranged in the lateral continuation of the second receiving space and thus contributes to safely holding the dental compound in the second receiving space.

Looking at a projected view of the projections of the first receiving space and second receiving space, the projections of the first receiving space can be at a lateral distance from the projections of the second receiving space. However, in order to ensure that the dental compound can be dispensed completely from the instrument head, it is preferable if, in a projected view, the projections of the first receiving space terminate with the projections of the second receiving space.

In order to further improve the hold of the dental compound, an intermediate projection can be arranged inside a receiving space, the surface area of which intermediate projection is small compared to the surface area of adjacent projections. If the intermediate projection projects further in the radial direction than do adjacent projections, it can be used to ensure that dental compound already dispensed from the receiving spaces is spread across the surface. If the receiving spaces in total extend all the way around a central support structure, it is possible, by turning the applicator instrument, to influence whether further dental compound is to be dispensed or the already dispensed dental compound is to be spread.

The dental compound should also be held safely in the applicator instrument when said applicator instrument is moved quickly. In the event of rapid movements of the applicator instrument, it may happen in particular that centrifugal forces oriented in the direction of the distal end of the applicator instrument act on the dental compound. Under the effect of such a centrifugal force, the dental compound is better held in the applicator instrument if the projections, in relation to their width extent, have a convexity directed toward the distal end.

Generally speaking, convexities in the height extent or width extent can contribute to providing the planar projections with greater stability. This may be helpful if the completely flat projections are able to deform too easily and greater stiffness is desired in order to be able to dispense the dental compound from the receiving space in dosed amounts.

The shaft can have one or more kinks. It is often easier to remove dental compound from a container when the shaft is straight, whereas it is easier to treat a hole in the tooth when the shaft is kinked. The shape of the shaft can preferably be plastically modified via the kinks.

The applicator instrument according to the invention can be produced in one piece, for example as an injection-molded part, from a single material. The property whereby the stiffness of the projections is less than the stiffness of the support structure is then achieved by virtue of the fact that the material thickness chosen for the support structure is greater than the material thickness of the projections. Alternatively, the applicator instrument can also be made from more than one material. For example, the support structure can be made from a material with greater stiffness and the projections can be made from a material with lesser stiffness. It is advantageous for the materials to be cohesively interconnected, as can be achieved, for example, in production by multi-component injection molding. A cohesive connection of this kind is more resistant than an adhesive connection obtained, for example, with glue.

A material connection that is resistant is particularly important if the instrument head is intended to be immersed for a considerable length of time in the dental compound. This is because the dental compounds often contain aggressive components that are able to undo adhesive connections. The applicator instrument according to the invention can be present as an applicator unit together with a container in which the dental compound is contained. The applicator instrument is then connected to the container such that the instrument head is arranged in the container and is immersed in the dental compound. After the container is opened, the applicator instrument is free and can be withdrawn. With conventional brushes or microbrushes in which the projections are connected adhesively to the support structure, this is not possible, because the adhesive connection may come undone under the effect of the aggressive dental compound.

BRIEF DESCRIPTION OF THE DRAWINGS

The invention is described below on the basis of an advantageous illustrative embodiment and with reference to the attached drawings, in which:

FIGS. 13 to 15 show various views of another embodiment of the invention; and

DETAILED DESCRIPTION OF THE INVENTION

Figure 1:
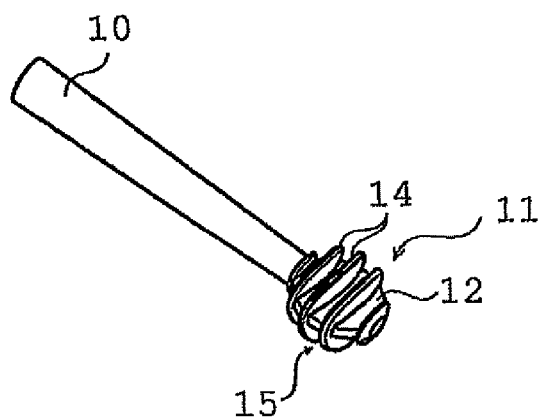
FIGS. 1 to 3 show various views of a first embodiment of an applicator instrument according to the invention.
Figures 2, 3:
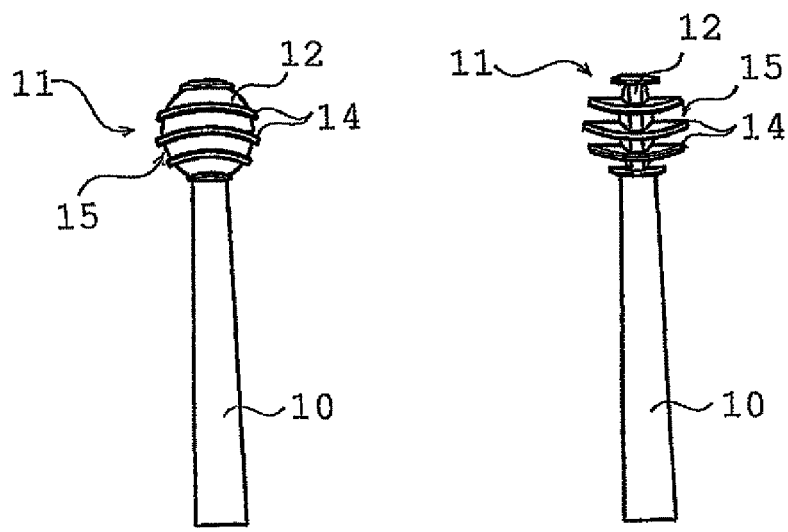

An applicator instrument shown in FIGS. 1 to 3 comprises a shaft 10 and an instrument head 11, which is connected to the distal end of the shaft 10. The instrument head 11 comprises a planar support structure 12, which has a circular contour. Five planar projections 14 are formed on each of the two sides of the support structure 12. The projections 14 have a height extent and a width extent. In height, the projections 14 run perpendicularly across the support structure 12. The width extent of the projections 14 is oriented transverse to the direction of the shaft 10. The projections 14 arranged at the center of the support structure 12 have a greater height, and the height of the projections 14 decreases in the direction toward the edge of the support structure 12. Each of the projections 14 has, in contour, the shape of a semicircle, with two opposite projections 14 complementing each other in terms of contour to form a complete circle. Overall, the support structure 12 and the projections 14 form a spherical shape in terms of their contour. The projections 14 have a convexity which is oriented toward the distal end of the applicator instrument and which runs across the width of the projections 14. The greatest diameter of the instrument head 11 is between 2 mm and 3 mm. The applicator instrument is therefore suitable for treating small holes in teeth.

The planar projections 14 are arranged substantially parallel to one another. Two adjacent projections 14 in each case enclose between them a receiving space 15. The receiving spaces 15 are limited on two opposite sides by the projections 14 and in addition by the support structure 12. In the other directions, the receiving spaces 15 open without restriction into the surrounding environment.

The applicator instrument is produced as a multi-component injection-molded part. The shaft 10 and the support structure 12 are made from a first material of greater stiffness, while the projections 14 are made from a second material, which is cohesively connected to the support structure 12 and which has less stiffness, i.e. greater flexibility.

The applicator instrument is intended to take up dental compounds from a storage container and to apply said dental compounds in a hole in a tooth. Here, the expression dental compound includes in particular dental adhesives, sealants, primers, and etching agents. The instrument head 11 of the applicator instrument is immersed into the dental compound in the storage container, such that the receiving spaces 15 fill with the dental compound. The size of the projections 14 and the distance of the projections 14 from one another are adapted to the properties of the dental compound. In the case of a dental compound of low viscosity, the projections 14 are at a smaller distance from one another, so as to ensure that they can hold the dental compound in the receiving spaces 15, and, in the case of viscous dental compounds, the distance between the projections 14 is greater.

Figure 4:
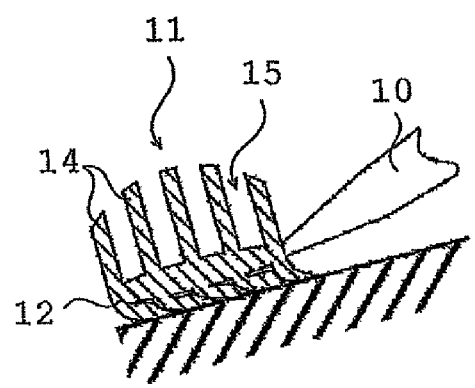
FIG. 4 shows the applicator instrument from FIGS. 1 to 3 with deformed projections.

When the receiving spaces 15 are filled with the dental compound, the instrument head 11 is lifted out of the storage container and guided to the tooth with the hole. By virtue of the convexity of the projections 14, the dental compound is held in the receiving spaces 15 even when the instrument head 12 is guided in a rapid movement. In the tooth, the dental compound should in the first instance be applied to the wall of the hole. For this purpose, the applicator instrument is initially placed with the projections 14 onto the wall of the hole. Pressure is then exerted via the support structure 12, such that the projections 14 deform as shown in FIG. 4. By means of the deformation of the projections 14, the volume of the receiving spaces 15 decreases and the dental compound emerges from the receiving spaces 15. With forward and backward strokes, the dental compound, initially applied only locally, can be spread across the surface. The projections have sufficient stiffness for the dental compound to be able to be spread across the surface, without this leading automatically to additional amounts of dental compound being applied.

Figure 5:
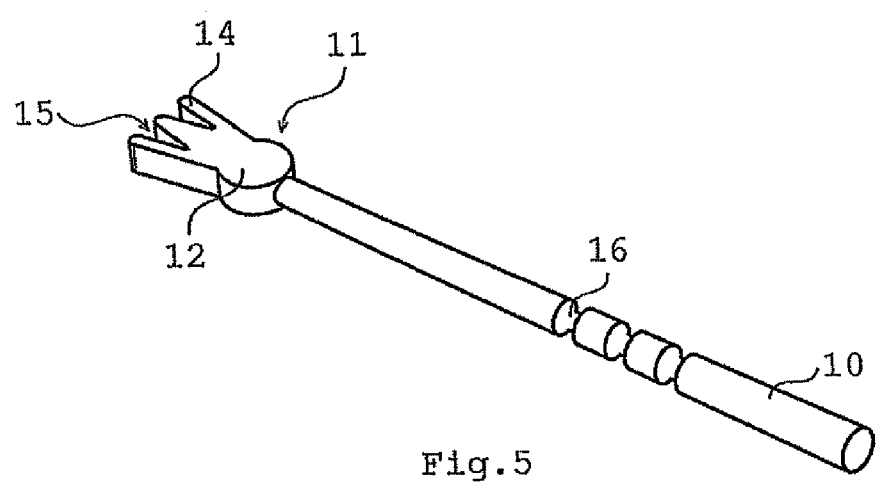
FIG. 5 shows a perspective view of another embodiment of an applicator instrument according to the invention.

The embodiment of an applicator instrument according to the invention shown in FIG. 5 comprises three projections 14 and, lying between these, receiving spaces 15. The shaft 10 is designed as a grip part with notches 16. The height extent of the projections 14 extends in a continuation of the shaft 10, while the width extent runs transverse to the direction of the shaft 10. The projections 14, in relation to their width extent, are parallel to one another and, in relation to their height extent, enclose a slight angle. The receiving spaces 15 thus have a slight V-shape in cross section. The applicator instrument is thus suitable for applying dental compounds to the end face of a hole. The dental compound can be dispensed from the receiving spaces 15 by pressure exerted in the direction of the shaft 10, and it can be spread by means of movements in the transverse direction thereto.

Figure 6:
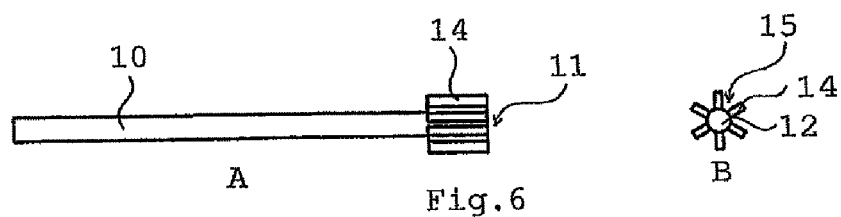
FIGS. 6 to 11 show various embodiments of applicator instruments according to the invention in a side view (A) and in a view in the axial direction (B)

In the applicator instrument in FIG. 6, the support structure 12 is cylindrical, and the height extent of the projections 14 runs in a radial direction from the support structure 12. The width extent of the projections 14 is oriented parallel to the shaft 10. By turning the applicator instrument about the axis of the shaft 10, the dental compound can be applied to the wall of a hole.

Figure 7:
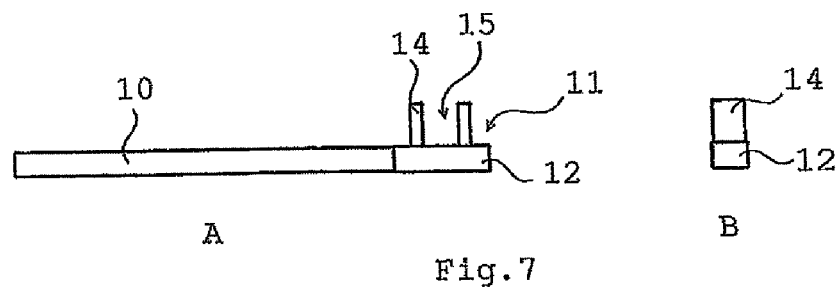

In the embodiment shown in FIG. 7, only two projections 14 are provided, with a receiving space 15 lying between them. The support structure 12 has a planar configuration in the shape of a rectangle. The height extent and the width extent of the projections 14 run transverse to the direction of the shaft 10. The distance between the projections 14 is almost as great as the height extent of the projections 14. The receiving space 15 thus formed is suitable for receiving rather viscous dental compounds.

Figure 8:
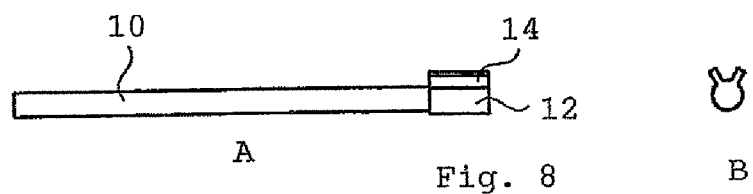

In the embodiment in FIG. 8, the support structure 12 is cylindrical. The height extent of the projections 14 is oriented radially, while the width extent is parallel to the direction of the shaft 10. The applicator instrument is produced as an injection-molded part from a single material. The reduced stiffness of the projections 14, compared to the support structure 12, is achieved by the fact that the projections 14 have a very small material thickness.

Figure 9:
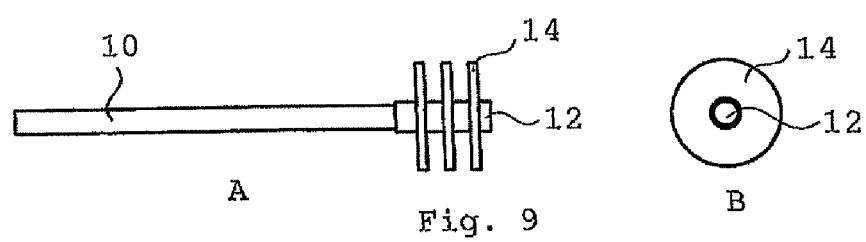
Figure 10:
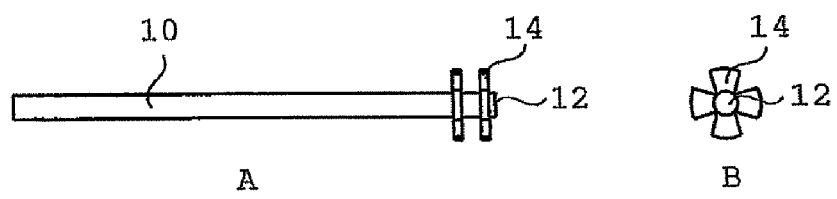
Figure 11:
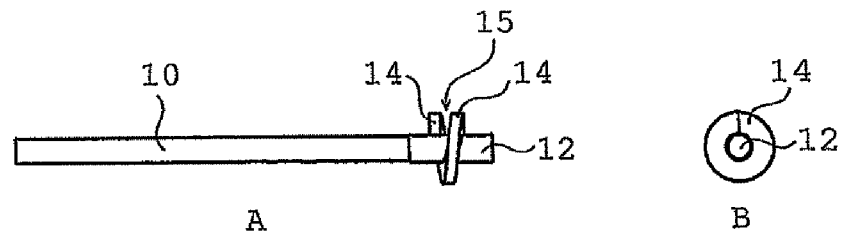

In FIG. 9, the projections 14 extend in a circle around the cylindrical support structure 12. The projections 14 are arranged parallel to one another and, in their height extent, run radially from the support structure 12. In the embodiment in FIG. 10, the projections are designed not in the form of closed circles, but in the form of interrupted circles. In FIG.

11, two projections delimiting a receiving space 15 are connected to each other in a spiral shape.

Figure 12:
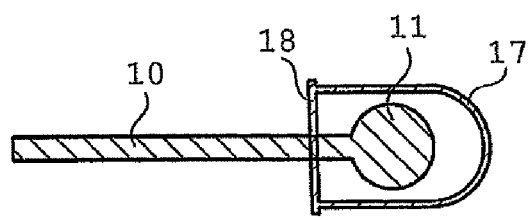
FIG. 12 shows an applicator unit made up of an applicator instrument according to the invention and of a container filled with a dental compound.

FIG. 12 shows an applicator unit comprising an applicator instrument according to the invention and a container 17 filled with dental compound. The applicator instrument is shown in a schematic representation, in which a spherical contour of the instrument head 11 is indicated. The shaft 10 of the applicator instrument extends through a lid 18 of the container 17. After the container 17 is opened, the applicator instrument can be removed, with the receiving compartments being filled with dental compound. Since the applicator instrument is either made from one uniform material or from several cohesively interconnected materials, it is not attacked by aggressive components of the dental compound.

FIGS. 13 to 15 show various views of an embodiment of the invention in which the receiving spaces are offset relative to one another. Thus, on one side of the applicator instrument, there are two projections 19, 20, which between them enclose a receiving space 21. On the other side of the applicator instrument, two projections 22, 23 are formed, which between them enclose a receiving space 24. The receiving spaces 21, 24 are offset relative to each other such that the projection 19 is arranged in the lateral continuation of the receiving space 24. Conversely, the projection 22 is arranged in the lateral continuation of the receiving space 21. This combination of receiving spaces offset relative to one another is repeated several times along the length of the instrument head 11. Altogether, the receiving spaces 21, 24 extend all the way around the central support structure. Seen in a projected view, the projections 19, 20 of the first receiving space 21 terminate with the projections 22, 23 of the second receiving space 24.

Arranged in the receiving space 24, there is an intermediate projection 25 whose surface area is smaller than the surface area of the projections 22, 23. However, the intermediate projection 25 projects further in the radial direction than do the projections 22, 23. In this embodiment, taking the receiving space 24 as an example, it is not only the adjacent projections 22, 23 by which the dental compound is held in the receiving space 24. Instead, the projection 19 lying in the lateral continuation of the receiving space 24 also contributes to holding the dental compound. The hold of the dental compound is further supported by the intermediate projection 25 arranged in the center of the receiving space 24. In relation to the volume encompassed by the projections, the instrument head 11 has a high absorption capacity for dental compound.

Figure 16:
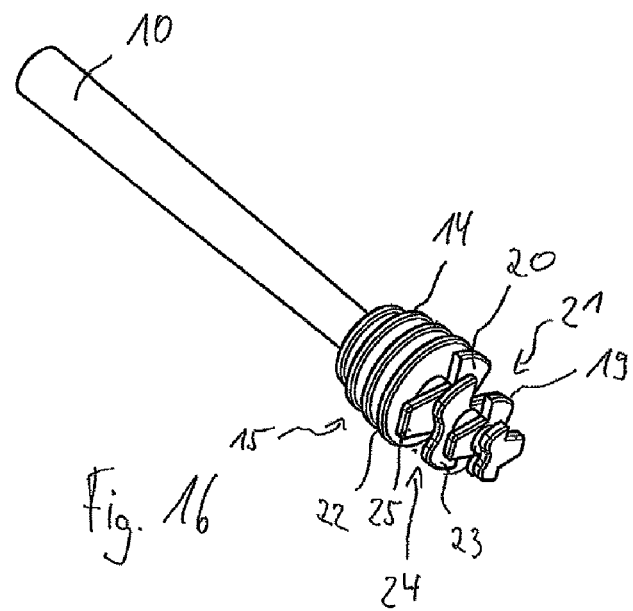
FIGS. 16 to 18 show various views of another embodiment of the invention.
Figures 17, 18:
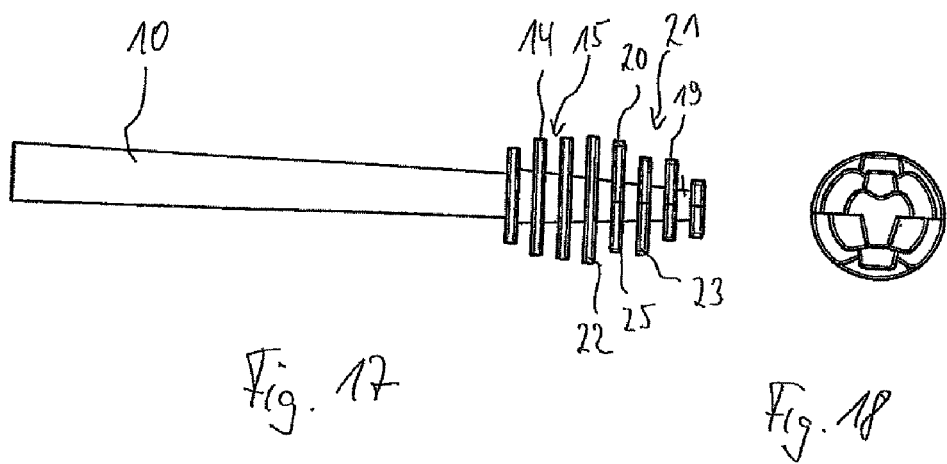

In the embodiment in FIGS. 16 to 18, projections 14 that extend all the way around the central support structure are formed in the rear area. Between them, the projections 14 enclose receiving spaces 15. In the front area, receiving spaces 21, 24 are formed which are offset relative to each other. The offset receiving spaces 21, 24 have the effect that, in relation to the volume encompassed by the instrument head, there is a high absorption capacity for the dental compound.

The invention claimed is:

1. An applicator instrument for applying a dental compound, comprising:
    a shaft;
    an instrument head being connected to a distal end of the shaft;
    a plurality of elastic projections formed on the instrument head,
    wherein the projections have a planar configuration and enclose a receiving space for the dental compound,
    wherein the shaft is made from a first material and the projections are made from a second material, the first material having a greater stiffness than the second material, and
    wherein the first material and the second material are cohesively interconnected and the cohesive interconnection between the first material and the second material is formed by multi-component injection molding.

2. The applicator instrument of claim 1, wherein the projections are arranged substantially parallel to one another with respect to a width extent.

3. The applicator instrument of claim 1, wherein the plurality of elastic projections includes more than two projections, enclosing a plurality of receiving spaces.

4. The applicator instrument of claim 3, wherein a first receiving space and a second receiving space are offset relative to each other such that a projection of the first receiving space is arranged in the lateral continuation of the second receiving space.

5. The applicator instrument of claim 4, wherein from a perspective of a projected view, projections of the first receiving space terminate with projections of the second receiving space.

6. The applicator instrument of claim 1, further comprising an intermediate projection arranged inside the receiving space, a surface area of the intermediate projection being small compared to the surface area of adjacent projections.

7. The applicator instrument of claim 6, wherein the intermediate projection projects further in the radial direction than do adjacent projections.

8. The applicator instrument of claim 1, wherein a portion of the shaft is configured as a grip part.

9. The applicator instrument of claim 1, wherein a height extent of the planar projections runs substantially transverse to the direction of the shaft.

10. The applicator instrument of claim 1, wherein the instrument head comprises a support structure, the support structure having a planar configuration.

11. The applicator instrument of claims 1, wherein the instrument head has an approximately spherical contour.

12. The applicator instrument of claim 1 wherein the receiving spaces occupy at least 40% of a volume encompassed by the instrument head.

13. The applicator instrument of claim 1 wherein the receiving spaces occupy at least 60% of a volume encompassed by the instrument head.

14. The applicator instrument of claim 1, wherein the greatest diameter of the instrument head is between 2 mm and 3 mm.

15. The applicator instrument of claim 1, wherein a width extent of the projections runs transverse to a longitudinal direction of the shaft and the projections have a convexity pointing in the direction of a distal end of the shaft.

16. An applicator unit, comprising:
    a container filled with a dental compound,
    the applicator instrument of claim 1,
    wherein the applicator instrument is connected to the container, and wherein the instrument head is immersed in the dental compound.

* * * * *